United States Patent
Jones et al.

(10) Patent No.: US 7,476,677 B2
(45) Date of Patent: Jan. 13, 2009

(54) SUBSTITUTED THIENO- AND THIAZOLO- [2,3-D]PYRIMIDINES AND [2,3-C]PYRIDINES AS INHIBITORS OF TIE2

(75) Inventors: Clifford David Jones, Macclesfield (GB); Richard William Arthur Luke, Macclesfield (GB); William McCoull, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/588,621

(22) PCT Filed: Feb. 1, 2005

(86) PCT No.: PCT/GB2005/000339

§ 371 (c)(1),
(2), (4) Date: Aug. 4, 2006

(87) PCT Pub. No.: WO2005/075483

PCT Pub. Date: Aug. 18, 2005

(65) Prior Publication Data

US 2007/0135455 A1    Jun. 14, 2007

(30) Foreign Application Priority Data

Feb. 5, 2004 (GB) .................. 0402518.5

(51) Int. Cl.
*C07D 495/04* (2006.01)
*A61K 31/519* (2006.01)

(52) U.S. Cl. .................. 514/258.1; 514/260.1; 544/255; 544/278

(58) Field of Classification Search .............. 544/255, 544/278; 514/260.1, 258.1
See application file for complete search history.

(56) References Cited

U.S. PATENT DOCUMENTS

2004/0014756 A1* 1/2004 Michaelides et al. ........ 514/241

FOREIGN PATENT DOCUMENTS

| WO | 1999/58523 A1 | 11/1991 |
| WO | 2002/062804 A1 | 8/2002 |
| WO | 2003/022852 A2 | 3/2003 |
| WO | 2003/055860 A1 | 7/2003 |
| WO | 2004/013141 A1 | 2/2004 |

* cited by examiner

*Primary Examiner*—Bruck Kifle

(57) ABSTRACT

A compound of the formula(I); wherein the substituents are as defined in the text for use in the production of an antiangiogenic effect in a warm blooded animal such as man. The compounds are inhibitors Tie2 receptor tyrosine kinase (TEK).

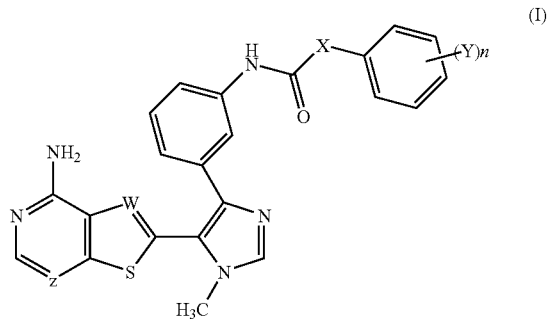

6 Claims, No Drawings

SUBSTITUTED THIENO- AND THIAZOLO- [2,3-D]PYRIMIDINES AND [2,3-C]PYRIDINES AS INHIBITORS OF TIE2

CROSS-REFERENCE TO RELATED APPLICATIONS

This application is a US National Stage under 35 U.S.C § 371 of International Application No. PCT/GB2005/000339 (filed Feb. 1, 2005) which claims priority under 35 U.S.C. § 119(a)-(d) to Application No. GB0402518.5 filed on Feb. 5, 2004.

This invention relates to compounds, or pharmaceutically acceptable salts thereof, which possess anti-angiogenic activity and are accordingly useful in methods of treatment of disease states associated with angiogenesis in the animal or human body. The invention also concerns processes for the preparation of the compounds, pharmaceutical compositions containing the compounds as active ingredient, and methods for the use of the compounds in the manufacture of medicaments for use in the production of anti-angiogenic effects in warm-blooded animals such as humans.

The Tie2 receptor tyrosine kinase (also known as TEK) is expressed predominantly in endothelial and haematopoietic cells and is essential for vessel formation and maintenance (Jones, N. et al. Nature Reviews Molecular Cell Biology. 2001: 2, 257-67).

Angiogenesis is a fundamental process defined as the generation of new blood vessels from existing vasculature. It is a vital yet complex biological process required for the formation and physiological functions of virtually all the organs. Normally it is transient in nature and is controlled by the local balance of angiogenic and angiostatic factors in a multi-step process involving vessel sprouting, branching and tubule formation by endothelial cells (involving processes such as activation of endothelial cells (ECs), vessel destabilisation, synthesis and release of degradative enzymes, EC migration, EC proliferation, EC organisation and differentiation and vessel maturation).

Normal angiogenesis plays an important role in a variety of processes and is under stringent control. In the adult, physiological angiogenesis is largely confined to wound healing and several components of female reproductive function and embryonic development. In undesirable or pathological angiogenesis, the local balance between angiogenic and angiostatic factors is dysregulated leading to inappropriate and/or structurally abnormal blood vessel formation. Pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacology. Science. 16: 57-66; Folkman, 1995, Nature Medicine 1: 27-31). In cancer, growth of primary and secondary tumours beyond 1-2 $mm^3$ requires angiogenesis (Folkman, J. New England Journal of Medicine 1995; 33, 1757-1763).

In diseases such as cancer in which progression is dependant on aberrant angiogenesis, blocking the process can lead to prevention of disease advancement (Folkman, J. 1995, Nature Medicine. 1: 27-31). Many factors are described in the scientific literature that are believed to play important critical roles in the regulation of angiogenesis. Two major classes of angiogenic factors are the vascular endothelial growth factor (VEGF) and the angiopoietins. These polypeptide moieties interact with their respective receptors (transmembrane tyrosine kinases which are predominantly endothelial cell specific) and induce cellular responses via ligand mediated signal transduction. It has been speculated that VEGF and the angiopoietins co-operate to regulate various aspects of the angiogenic process during both normal and pathological angiogenesis via signalling through their respective receptors.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

Recently a second family of predominantly endothelial cell specific receptors that regulate vessel destabilisation and maturation have been identified. The Tie receptors and their ligands, the angiopoietins, co-operate closely with VEGF during both normal and pathological angiogenesis. The transmembrane receptors Tie1 and Tie2, constitute a family of endothelial cell specific tyrosine kinase receptors involved in maintenance of blood vessel integrity and which are involved in angiogenic outgrowth and vessel remodelling. Structurally Tie1 and Tie2 share a number of features (e.g. the intracellular domains of both these receptors each contain a tyrosine kinase domain interrupted by a kinase insert region) and thus constitute a distinct RTK subfamily. Overall sequence identity between Tie1 and Tie2 receptors at the amino acid level is 44% while their intracellular domains exhibit 76% homology. Targeted disruption of the Tie1 gene results in a lethal phenotype characterised by extensive haemorrhage and poor microvessel integrity (Puri, M. et al. 1995 EMBO Journal:14: 5884-5891). Transgenic mice deficient in Tie2 display defects in vessel sprouting and remodelling and display a lethal phenotype in mid gestation (E9.5-10.5) caused by severe defects in embryonic vasculature (Sato, T. et al. 1995 Nature 370: 70-74).

To date no ligands have been identified for Tie1 and little is known regarding its signalling abilities. However, Tie1 is believed to influence Tie2 signalling via heterodimerisation with the Tie2 receptor (hence potentially modulating the ability of Tie2 to autophosphorylate (Marron, M. et al. 2000 Journal of Biological Chemistry: 275, 39741-39746) and recent chimaeric Tie1 receptor studies have indicated that Tie-1 may inhibit apoptosis via the PI 3 kinase/Akt signal transduction pathway (Kontos, C. D., et al., 2002 Molecular and Cellular Biology: 22, 1704-1713). In contrast, a number of ligands, designated the angiopoietins have been identified for Tie2 of which Angiopoietin 1 (Ang1) is the best characterised. Binding of Ang1 induces tyrosine phosphorylation of the Tie2 receptor via autophosphorylation and subsequently activation of its signalling pathways via signal transduction. Ang2 has been reported to antagonise these effects in endothelial cells (Maisonpierre, P. et al. 1997 Science: 277, 55-60). The knock-out and transgenic manipulation of Tie2 and its ligands suggest that stringent spatial and temporal control of Tie2 signalling is imperative for the correct development of new vasculature. There are also reports of at least another two ligands (Ang3 and Ang4) as well as the possibility of heterodimerisation between the angiopoietin ligands that has the potential to modify their activity (agonistic/antagonistic) on association with the receptor. Activation of the Tie2 receptor by Ang1 inhibits apoptosis (Papapetropoulos, A., et al., 2000 Journal of Biological Chemistry: 275 9102-9105), promotes sprouting in vascular endothelial cells (Witzenbicher, B., et al., 1998 Journal of Biological Chemistry: 273, 18514-18521) and in vivo promotes blood vessel maturation during angiogenesis and reduces the permeability and consequent leakage from adult microvessels (Thurston, G. et al., 2000 Nature Medicine: 6, 460-463). Thus activated Tie2 receptor is reported to be involved in the branching, sprouting and outgrowth of new vessels and recruitment and interaction of periendothelial support cells important in maintaining vessel integrity and overall appears to be consistent with promoting microvessel stability. Absence of Tie2 activation or inhibition of Tie2 auto phosphorylation may lead to a loss of vascular structure and matrix/cell contacts (Brindle, N., in press, 2002) and in turn may trigger endothelial cell death, especially in the absence of survival or growth stimuli. On the basis of the above reported effects due to Tie2 kinase activity, inhibiting Tie2 kinase may provide an anti-angiogenic effect and thus have application in the therapy of disease states associated with pathological angiogenesis. Tie2 expression has been shown to be up-regulated in the neovasculature of a variety of tumours (e.g. Peters, K. G. et al, (British Journal of Cancer 1998; 77,51-56) suggesting that inhibiting Tie2 kinase activity will result in anti-angiogenic activity. In support of this hypothesis, studies with soluble Tie2 receptor (extracellular domain) (Pengnian, L. et al., 1997, Journal of Clinical Investigation 1997: 100, 2072-2078 and Pengnian, L. et al., 1998, Proceedings of the National Academy of Sciences 1998: 95, 8829-8834) have shown anti-tumour activity in in vivo tumour models. In addition these experiments also indicate that disruption of the Tie2 signalling pathways in a normal healthy individual may be well tolerated as no adverse toxicities were observed in these studies.

Examination of human primary breast cancer samples and human and murine breast cancer cell lines (Stratmann, A., et al., 2001, International Journal of Cancer: 91,273-282) indicate that Tie2 dependant pathways of tumour angiogenesis may exist alongside KDR dependant pathways and, in fact, may operate both independently (Siemeister G., et al., 1999 Cancer Research: 59,3185-3191) as well as in concert with each other (e.g. VEGF A and Ang1 reported to collaborate to induce angiogenesis and produce non-leaky mature vessels Thurston, G, et al., 1999 Science: 286,2511-2514). It is quite possible that a mix of such angiogenic processes even exist within a single tumour.

Tie2 has also been shown to play a role in the vascular abnormality called venous malformation (VM) (Mulliken, J. B. & Young, A. E. 1998, Vascular Birthmarks: W. B. Saunders, Philadelphia). Such defects can either be inherited or can arise sporadically. VM's are commonly found in the skin or mucosal membranes but can affect any organ. Typically lesions appear as a spongy, blue to purple vascular masses composed of numerous dilated vascular channels lined by endothelial cells. Among the inherited forms of this disease the most common defect appears to be a Tie2 kinase mutation C2545T in the Tie2 coding sequence (Calvert, J. T., et al., 1999 Human Molecular genetics: 8, 1279-1289), which produces a R849W amino acid substitution in the kinase domain. Analysis of this Tie2 mutant indicates that it is constitutively activated even in the absence of ligand (Vikkula, M., et al., 1996 Cell: 87,1181-1190).

Upregulation of Tie2 expression has also been found within the vascular synovial pannus of arthritic joints in humans, which is consistent with the role of inappropriate neovascularisation.

Such examples provide further indications that inhibition of Tie2 phosphorylation and subsequent signal transduction will be useful in treating disorders and other occurrences of inappropriate neovascularisation. To date only a few inhibitors of Tie2 are known in the art. There is thus a need to identify additional Tie2 inhibitors that could exploit the full therapeutic potential of inhibiting/modulating the Tie2 signalling pathways.

We have found that certain compounds possess inhibitory activity for the Tie2 receptor tyrosine kinase and accordingly have value in the treatment of disease states associated with pathological angiogenesis such as cancer, rheumatoid arthritis, and other diseases where active angiogenesis is undesirable.

According to a first aspect of the present invention, there is provided a compound of the formula I:

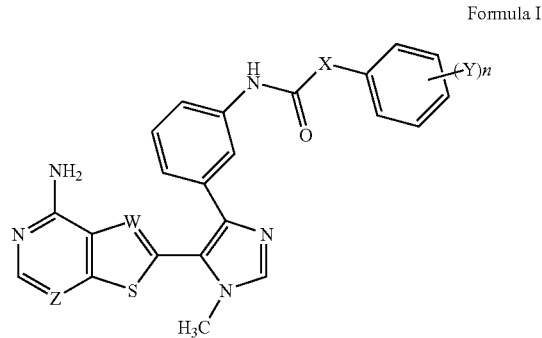

Formula I wherein:
Z is selected from N and CH;
W is selected from N and CH;
X is selected from NH and $CH_2$;
Y is selected from F, Cl, Br and I; and
n is 1, 2 or 3;

and salts or solvates thereof (particularly pharmaceutically acceptable salts thereof).

According to a second aspect of the present invention, there is provided a compound of the formula I:

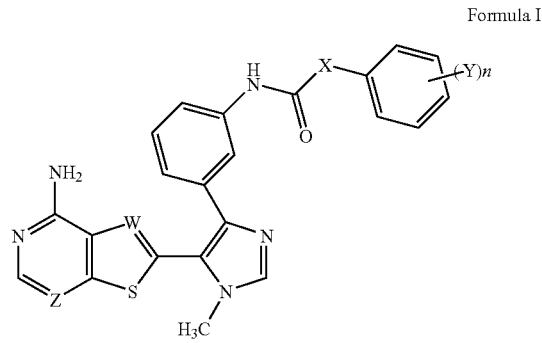

Formula I wherein:
Z is N;
W is selected from N and CH;
X is selected from NH and CH$_2$;
Y is selected from F, Cl, Br and I; and
n is 1, 2 or 3;

and salts or solvates thereof (particularly pharmaceutically acceptable salts thereof).

Particular compounds of the present invention include, for example, compounds of the formula I, or salts or solvates thereof (particularly pharmaceutically acceptable salts thereof), wherein Z is N, W is N and X, Y and n are as hereinbefore defined. Further particular compounds of the present invention include, for example, compounds of the formula I, or salts or solvates thereof (particularly pharmaceutically acceptable salts thereof), wherein Z is N, W is CH and X, Y and n are as hereinbefore defined.

According to a third aspect of the present invention, there is provided a compound of the formula I:

Formula I

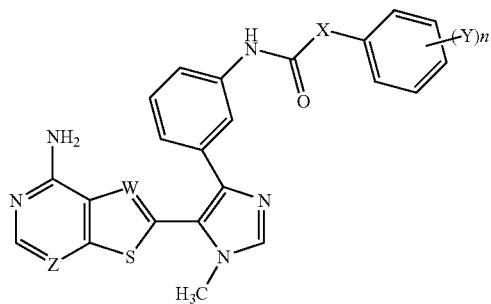

wherein:
Z is selected from N and CH;
W is N;
X is selected from NH and CH$_2$;
Y is selected from F, Cl, Br and I; and
n is 1, 2 or 3;

and salts or solvates thereof (particularly pharmaceutically acceptable salts thereof).

Particular compounds of the present invention include, for example, compounds of the formula I, or salts or solvates thereof (particularly pharmaceutically acceptable salts thereof), wherein Z is CH, W is N and X, Y and n are as hereinbefore defined.

According to a fourth aspect of the present invention, there is provided a compound of the formula I:

Formula I

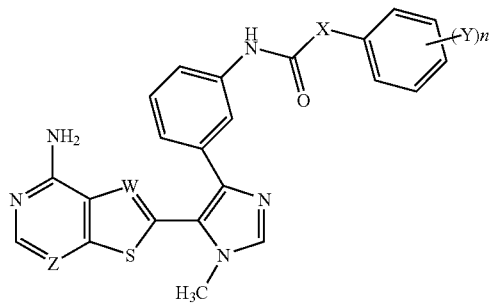

wherein:
Z is selected from N and CH;
W is CH;
X is selected from NH and CH$_2$;
Y is selected from F, Cl, Br and I; and
n is 1, 2 or 3;

and salts or solvates thereof (particularly pharmaceutically acceptable salts thereof).

Particular compounds of the present invention include, for example, compounds of the formula I, or salts or solvates thereof (particularly pharmaceutically acceptable salts thereof), wherein Z is CH, W is CH and X, Y and n are as hereinbefore defined.

As stated above, in the compounds of the present invention, Y is selected from fluoro, chloro, bromo and iodo, particularly selected from fluoro and chloro.

It should be understood that when n is 2 or 3 that Y may be the same or different.

Specific compounds of the present invention are one or more of the following:

N-{3-[5-(4-aminothieno[2,3-d]pyrimidin-6-yl)-1-methyl-1H-imidazol-4-yl]phenyl}-N'-(3-fluorophenyl)urea N-{3-[5-(4-aminothieno[2,3-d]pyrimidin-6-yl)-1-methyl-1H-imidazol-4-yl]phenyl}-N'-(2-fluorophenyl)urea N-{3-[5-(4-aminothieno[2,3-d]pyrimidin-6-yl)-1-methyl-1H-imidazol-4-yl]phenyl}-N'-(3-chlorophenyl)urea N-{3-[5-(4-aminothieno[2,3-d]pyrimidin-6-yl)-1-methyl-1H-imidazol-4-yl]phenyl}-N'-(2-chlorophenyl)urea N-{3-[5-(4-aminothieno[2,3-d]pyrimidin-6-yl)-1-methyl-1H-imidazol-4-yl]phenyl}-2-(3-fluorophenyl)acetamide N-{3-[5-(4-aminothieno[2,3-d]pyrimidin-6-yl)-1-methyl-1H-imidazol-4-yl]phenyl}-2-(2-fluorophenyl)acetamide N-{3-[5-(4-aminothieno[2,3-d]pyrimidin-6-yl)-1-methyl-1H-imidazol-4-yl]phenyl}-2-(3-chlorophenyl)acetamide N-{3-[5-(4-aminothieno[2,3-d]pyrimidin-6-yl)-1-methyl-1H-imidazol-4-yl]phenyl}-2'-(2-chlorophenyl)acetamide N-{3-[5-(4-aminothiazolo[2,3-d]pyrimidin-6-yl)-1-methyl-1H-imidazol-4-yl]phenyl}-N'-(3-fluorophenyl)urea N-{3-[5-(4-aminothiazolo[2,3-d]pyrimidin-6-yl)-1-methyl-1H-imidazol-4-yl]phenyl}-N'-(2-fluorophenyl)urea N-{3-[5-(4-aminothiazolo[2,3-d]pyrimidin-6-yl)-1-methyl-1H-imidazol-4-yl]phenyl}-N'-(3-chlorophenyl)urea N-{3-[5-(4-aminothiazolo[2,3-d]pyrimidin-6-yl)-1-methyl-1H-imidazol-4-yl]phenyl}-N'-(2-chlorophenyl)urea N-{3-[5-(4-aminothiazolo[2,3-d]pyrimidin-6-yl)-1-methyl-1H-imidazol-4-yl]phenyl}-2-(3-fluorophenyl)acetamide N-{3-[5-(4-aminothiazolo[2,3-d]pyrimidin-6-yl)-1-methyl-1H-imidazol-4-yl]phenyl}-2-(2-fluorophenyl)acetamide N-{3-[5-(4-aminothiazolo[2,3-d]pyrimidin-6-yl)-1-methyl-1H-imidazol-4-yl]phenyl}-2-(3-chlorophenyl)acetamide N-{3-[5-(4-aminothiazolo[2,3-d]pyrimidin-6-yl)-1-methyl-1H-imidazol-4-yl]phenyl}-2-(2-chlorophenyl)acetamide and salts or solvates thereof (particularly pharmaceutically acceptable salts thereof).

A suitable pharmaceutically-acceptable salt of a compound of the formula I is, for example, an acid-addition salt of a compound of the formula I, for example an acid-addition salt with an inorganic or organic acid such as hydrochloric, hydrobromic, sulfuric, trifluoroacetic, citric or maleic acid; or, for example, a salt of a compound of the formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

It is to be understood that, insofar as certain of the compounds of formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of the formula I may exist in solvated as well as unsolvated forms such as, for example, hydrated forms. It is to be understood that the invention encompasses all such solvated forms which exhibit an inhibitory effect on a Tie2 receptor tyrosine kinase.

It is also to be understood that certain compounds of the formula I may exhibit polymorphism, and that the invention encompasses all such forms which exhibit an inhibitory effect on a Tie2 receptor tyrosine kinase.

It is also to be understood that the invention relates to all tautomeric forms of the compounds of the formula I forms which exhibit an inhibitory effect on a Tie2 receptor tyrosine kinase.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

Also provided as a further aspect of the invention are pro-drugs of compounds of the invention as herein before or herein after defined. Compounds of the invention may be administered in the form of a pro-drug which is broken down in the human or animal body to give a compound of the Formula (I). Examples of pro-drugs include in-vivo hydrolysable amides of a compound of the Formula (I).

Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

A compound of formula I, or a pharmaceutically acceptable salt thereof, may be prepared by any process known to be applicable to the preparation of chemically-related compounds. Such processes, when used to prepare a compound of formula I are provided as a further feature of the invention and are illustrated by the following representative process variants. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated, which are within the ordinary skill of an organic chemist.

According to a further aspect, the present invention provides a process for preparing a compound of formula I, or a pharmaceutically acceptable salt thereof, wherein X is NH and Z, W, Y and n are as defined in formula I, which process comprises of reacting an amine of the formula II with an isocyanate of the formula III

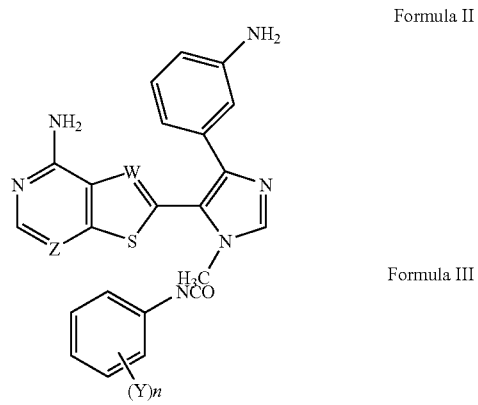

and thereafter if necessary:
i) converting a compound of the formula (I) into another compound of the formula (I);
ii) forming a salt or solvate.

The aforementioned process is conveniently carried out in a suitable inert solvent or diluent such as an ether, for example tetrahydrofuran, DMF, DCM, DMA or pyridine. The process is preferably carried out at a temperature of less than 50° C., for example 0 to 30° C., preferably at ambient temperature.

The amine of the formula II may be prepared by the reaction scheme (i) below:

Scheme (i)

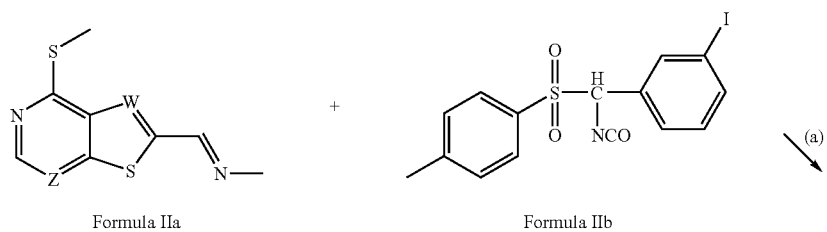

-continued

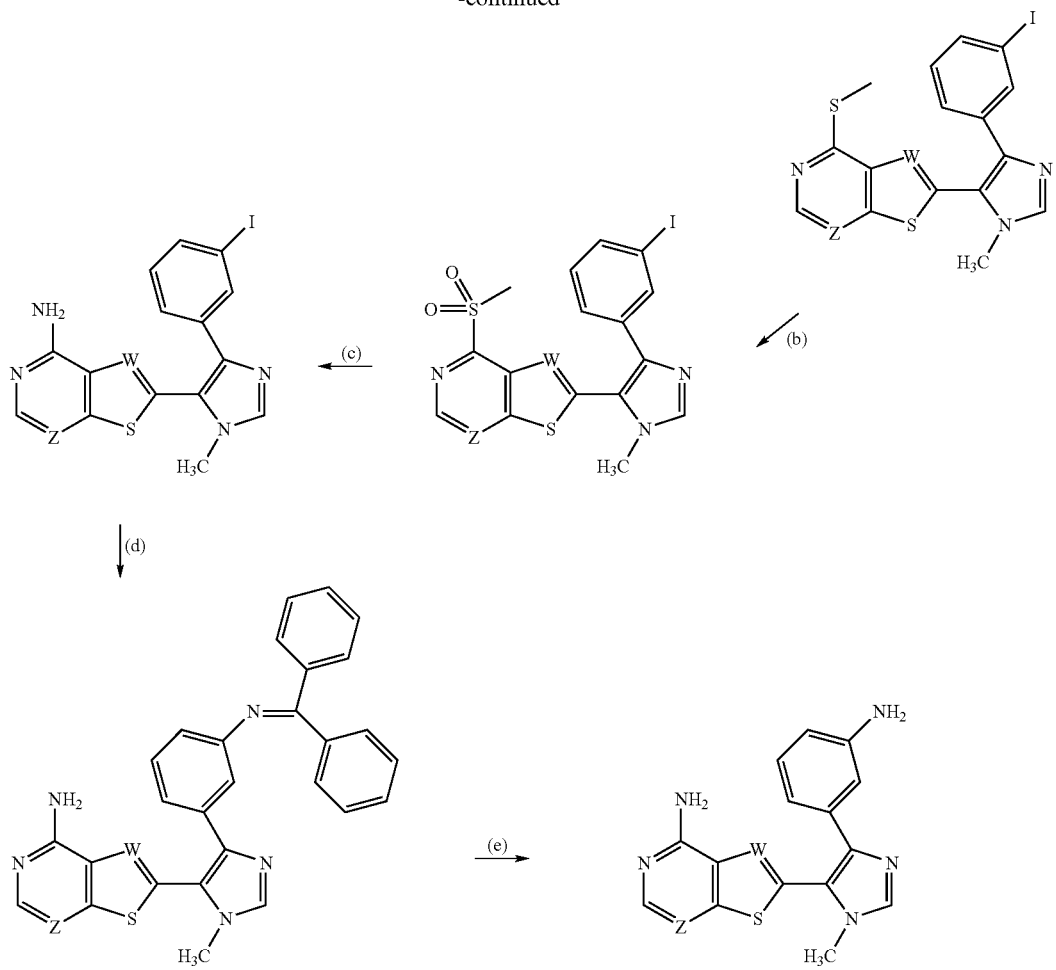

Formula II wherein:
(a) Piperazine in THF
(b) m-CPBA in DCM
(c) Concentrated aqueous ammonia in 1,4-dioxane
(d) Benzophenone imine, 1,1'-bis(diphenylphosphino)ferrocene, bis(benzylideneacetone)palladium and sodium tert-butoxide in dioxane
(e) HCl in THF The compound of the formula IIa may be prepared by the reaction scheme (ii) below:

Scheme (ii)

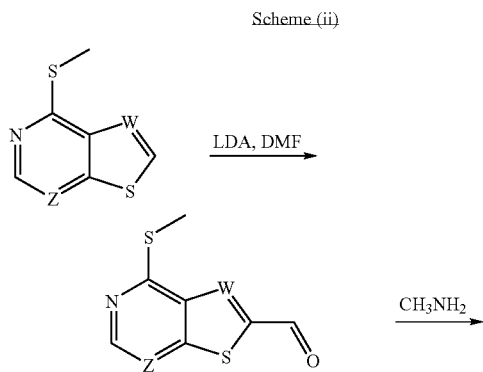

-continued

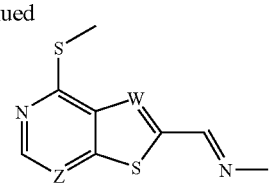

Formula IIa

The sulfone of the formula IIb may be prepared by the reaction of trimethylsilylchloride, 3-iodobenzaldehyde, formamide and toluene sulphinic acid to produce {(3-iodophenyl)[(4-methylphenyl)sulphonyl]methyl}formamide and then the reaction of the {(3-iodophenyl)[(4-methylphenyl)sulphonyl]methyl}formamide with phosphorus oxychloride to produce the sulfone of the formula IIb.

According to another aspect, the present invention provides a process for preparing a compound of formula I, or a pharmaceutically acceptable salt thereof, wherein X is $CH_2$ and Z, W, Y and n are as defined in formula I, which process comprises of reacting an amine of the formula II with an appropriate acyl chloride or acyl ester, as the skilled person would appreciate.

When a pharmaceutically acceptable salt of a compound of formula I is required, for example an acid addition salt, it may be obtained by, for example reaction of a compound of the formula I with a suitable acid such as hydrochloric acid, using a conventional procedure. When the free-base form of the compound of formula I is required an acid addition salt of the compound of formula I may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Certain compounds of formula I are capable of existing in stereoisomeric forms. It will be understood that the invention encompasses all geometric and optical isomers of the compounds of formula I and mixtures thereof including racemates. Tautomers and mixtures thereof also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral High Performance Liquid Chromatography (HPLC)). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

It will be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example -methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

It will also be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. A particular example of an aromatic substitution reaction includes the introduction of a halogeno group.

Biological Assays

The following assays can be used to measure the effects of the compounds of the present invention as Tie2 inhibitors in vitro and as inhibitors of Tie2 autophosphorylation in whole cells.

a. In Vitro Receptor Tyrosine Kinase Inhibition Assay

To test for inhibition of Tie2 receptor tyrosine kinase, compounds are evaluated in a non-cell based protein kinase assay by their ability to inhibit the protein kinase enzyme phosphorylation of a tyrosine containing polypeptide substrate in an ELISA based microtitre plate assay. In this particular case, the assay was to determine the $IC_{50}$, for three different recombinant human tyrosine kinases Tie2, KDR and Flt.

To facilitate production of the tyrosine kinases, recombinant receptor genes were produced using standard molecular biology cloning and mutagenesis techniques. These recombinant proteins fragments encoded within these genes consist of only the intracellular portion C-terminal portion of the respective receptor, within which is found the kinase domain. The recombinant genes encoding the kinase domain containing fragments were cloned and expressed in standard baculovirus/Sf21 system (or alternative equivalent).

Lysates were prepared from the host insect cells following protein expression by treatment with ice-cold lysis buffer (20 mM N-2-hydroxyethylpiperizine-N'-2-ethanesulphonic acid (HEPES) pH 7.5, 150 mM NaCl, 10% glycerol, 1% Triton X-100, 1.5 mM $MgCl_2$, 1 mM ethylene glycol-bis (β-aminoethyl ether) N',N',N',N'-tetraacetic acid (EGTA), plus protease inhibitors and then cleared by centrifugation. Tie2, KDR and Flt1 lysates were stored in aliquots at −80° C.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Nunc Maxisorb™ 96-well immunoplates were coated with 100 microlitres of synthetic peptide Sigma P3899 (1 mg/ml stock solution in PBS diluted 1:500 in PBS prior to plate coating) and incubated at 4° C. overnight. Plates were washed in 50 mM HEPES pH 7.4 at room temperature to remove any excess unbound synthetic peptide.

Tie2, KDR or Flt1 activities were assessed by incubation of the appropriate freshly diluted lysates (1:200, 1:400 and 1:1000 respectively) in peptide coated plates for 60 minutes (Tie2) or 20 minutes for (KDR, Flt) at room temperature in 100 mM HEPES pH 7.4, adenosine trisphosphate (ATP) at 5 micromolar (or Km concentration for the respective enzyme, 10 mM $MnCl_2$, 0.1 mM $Na_3VO_4$, 0.2 mM DL-dithiothreitol (DTT), 0.1% Triton X-100 together with the test compound(s) in dissolved in DMSO (final concentration of 2.5%) with final compound concentrations ranging from 0.05 micromolar-100 micromolar. Reactions were terminated by the removal of the liquid components of the assay followed by washing of the plates with PBS-T (phosphate buffered saline with 0.5% Tween 20) or an alternative equivalent wash buffer.

The immobilised phospho-peptide product of the reaction was detected by immunological methods. Firstly, plates were incubated for 4 hours at room temperature with murine monoclonal anti-phosphotyrosin —HRP (Horseradish Peroxidase) conjugated antibodies (4G10 from Upstate Biotechnology UBI 16-105). Following extensive washing with PBS-T, HRP activity in each well of the plate was measured colorimetrically using 22'-Azino-di-[3-ethylbenzthiazoline sulfonate (6)] diammonium salt crystals ABTS (Sigma P4922—prepared as per manufactures instructions) as a substrate incubated for 30-45 minutes to allow colour development, before 100 ul of 1M H2SO4 was added to stop the reaction.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b. Cellular Tie2 Autophosphorylation Assay

This assay is based on measuring the ability of compounds to inhibit autophosphorylation of the Tie2 receptor which normally leads to the production of "activated" receptor that in turn initiates the particular signal transduction pathways associated with the receptor function.

Autophosphorylation can be achieved by a number of means. It is known that expression of recombinant kinase domains in baculoviral systems can lead to the production of phosphorylated and activated receptor. It is also reported that over expression of receptors in recombinant cell lines can itself lead to receptor autophosphorylation in the absence of the ligand (Heldin C-H. 1995 Cell: 80, 213-223; Blume-J. P, Hunter T. 2001 Nature: 411, 355-65). Furthermore, there are numerous literature examples in which chimaeric receptors have been constructed. In these cases the natural, external cell surface domain of the receptor has been replaced with that of a domain which is known to be readily dimerised via the addition of the appropriate ligand (e.g. TrkA-Tie2/NGF ligand (Marron, M. B., et al., 2000 Journal of Biological Chemistry: 275:39741-39746) or C-fms-Tie-1/CSF-1 ligand (Kontos, C. D., et al., 2002 Molecular and Cellular Biology: 22, 1704-1713). Thus when the chimaeric receptor expressed in a host cell line and the respective ligand is added, this induces autophosphorylation of the chimeric receptor's kinase domain. This approach has the advantage of often allowing a known (and often easily obtained) ligand to be used instead of having to identify and isolate the natural ligand for each receptor of interest.

Naturally if the ligand is available one can use natural cell lines or primary cells which are known to express the receptor of choice and simply stimulate with ligand to achieve ligand induced phosphorylation. The ability of compounds to inhibit autophosphorylation of the Tie2 receptor, which is expressed for example in EA.hy926/B3 cells (supplied by J. McLean/B. Tuchi, Univ. of N. Carolina at Chapel Hill, CB-4100, 300 Bynum Hall, Chapel Hill, N.C. 27599-41000, USA) or primary HUVEC (human umbilical vein endothelial cells—available from various commercial sources), can be measured by this assay.

Natural Ang1 ligand can be isolated using standard purification technology from either tumour cell supernatants or alternatively the Ang1 gene can be cloned and expressed recombinantly using stand molecular biology techniques and expression systems. In this case one can either attempt to produce the ligand either in its native state or as recombinant protein which for example may have been genetically engineered to contain additional of purification tags (eg. polyhistidine peptides, antibody Fc domains) to facilitate the process.

Using the ligand stimulation of either EA.hy926/B3 or HUVEC cellular Tie2 receptor as the example, a Ang1 ligand stimulated cellular receptor phosphorylation assay can be constructed which can be used to analyse to determine the potential of compounds to inhibit this process. For example EA.hy926/B3 cells were grown in the appropriate tissue culture media plus 10% foetal calf serum (FCS) for two days in 6 well plates starting with an initial seeding density of 5×10$^5$ cells/well. On the third day the cells were serum starved for a total of 2 hours by replacing the previous media with media containing only 1% FCS. After 1 hour 40 minutes of serum starvation the media was removed and replace with 1 ml of the test compound dilutions (compound dilutions made in serum starvation media yet keeping the DMSO concentration below 0.8%). After 1.5 hours of serum starvation orthovanidate was added to a final concentration of 0.1 mM for the final 10 minutes of serum starvation.

Following a total of 2 hours of serum starvation, the ligand plus orthovandiate was added to stimulate autophosphorylation of the cellular Tie2 receptor (ligand can be added either as purified material diluted in serum starvation media or non-purified cell supernatant containing ligand e.g. when recombinantly expressed mammalian cells).

After 10 minutes incubation at 37° C. with the ligand, the cells were cooled on ice washed with approximately 5 mls with cold PBS containing 1 mM orthovanadate, after which 1 ml of ice cold lysis buffer ((20 mM Tris pH 7.6, 150 mM NaCl, 50 mM NaF, 0.1% SDS, 1% NP40, 0.5% DOC, 1 mM orthovanadate, 1 mM EDTA, 1 mM PMSF, 30 µl/ml Aprotinin, 10 µg/ml Pepstatin, 10 µg/ml Leupeptin) was added the cells and left on ice for 10-20 minutes. The lysate was removed and transferred to a 1.5 ml Eppendorf tube and centrifuged for 3 minutes at 13000 rpm at 4° C. 800 µl of each lysate was transferred to fresh 2 ml Eppendorf tubes for the immuno-precipitation. 3 mg=15 µl of anti-phospho-tyrosine antibody (Santa Cruz PY99-sc-7020) was added to the lysates and left to incubate for 2 hours at 4° C. 600 µl washed MagnaBind beads (goat anti-mouse IgG, Pierce 21354) were added to the lysates and the tubes left to rotate over night at 4° C.

Samples were treated for 1 minute in the magnet before carefully removing the lysis supernatant. 1 ml of lysis buffer was then added to the beads and this step repeated twice more. The beads were suspended in 25 µl of 94° C. hot 2× Laemmli loading buffer plus beta-mercaptoethanol and left to stand for 15 minutes at room temperature.

The beads were removed by exposing the tubes for 1 minute in the magnet, and the total liquid separated from the beads from each immuno-precipitate loaded onto Polyacrylamide/SDS protein gels (pre-cast 4-12% BisTris NuPAGE/MOPS 12 well gels from Novex). Protein gels were run at 200 V and then blotted onto NC membrane for 1 hours 30 minutes at 50 V/250 mA. All blots were treated with 5% Marvel in PBS-Tween for 1 hour at room temperature to reduce non-specific binding of the detection antibody. A rabbit anti-Tie2 (Santa Cruz sc-324) was added in a 1:500 dilution in 0.5% Marvel/PBS-Tween and left to incubate overnight at 4° C. The blots were rigorously washed with PBS-Tween before adding the goat anti rabbit-POD conjugate (Dako P0448) at a 1:5000 dilution in 0.5% Marvel/PBS-Tween. The antibody was left on for 1 hour at room temperature before subsequently washing the blots with PBS-Tween. The western blots of the various immuno-precipitated samples were developed the blots with LumiGLO (NEB 7003) and transferred to an X-Ray cassette and films exposed for 15 sec/30 sec and 60 sec. The relative strength of the protein band which pertains to the phosphorylated Tie2 receptor was evaluated using a FluorS BioRad image analyser system. The percentage phosphorylation for each test compound dilution series was determined from which $IC_{50}$ values were calculated by standard methods using the appropriate control samples as reference.

Although the pharmacological properties of the compounds of the formula I vary with structural change as expected, in general activity possessed by compounds of the formula I, may be demonstrated at the following concentrations or doses in one or more of the above tests (a) and (b):—

Test (a):—$IC_{50}$ in the range, for example, <100 µM;
Test (b):—$IC_{50}$ in the range, for example, <50 µM;
For example, Example 1 had an $IC_{50}$ of 16 µM in Test (a) and an $IC_{50}$ of 0.4 µM in Test (b).

According to a further aspect of the invention there is provided a pharmaceutical composition which comprises a compound of the formula I, or a pharmaceutically acceptable salt thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the formula I for therapeutic or prophylactic purposes it will generally be administered so that a daily dose in the range, for example, 0.1 mg/1(g to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

The compounds according to the present invention as defined herein are of interest for, amongst other things, their antiangiogenic effect. The compounds of the invention are expected to be useful in the treatment or prophylaxis of a wide range of disease states associated with undesirable or pathological angiogenesis, including cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. Cancer may affect any tissue and includes leukaemia, multiple myeloma and lymphoma. In particular such compounds of the invention are expected to slow advantageously the growth of primary and recurrent solid tumours of, for example, the colon, breast, prostate, lungs and skin.

We believe that the antiangiogenic properties of the compounds according to the present invention arise from their Tie2 receptor tyrosine kinase inhibitory properties. Accordingly, the compounds of the present invention are expected be useful to produce a Tie2 inhibitory effect in a warm-blooded animal in need of such treatment. Thus the compounds of the present invention may be used to produce an antiangiogenic effect mediated alone or in part by the inhibition of Tie2 receptor tyrosine kinase.

More particularly the compounds of the invention are expected to inhibit any form of cancer associated with Tie2. For example, the growth of those primary and recurrent solid tumours which are associated with Tie2, especially those tumours which are significantly dependent on Tie2 receptor tyrosine kinase for their growth and spread.

According to a further aspect of the invention there is provided a compound of the formula I, or a pharmaceutically acceptable salt thereof, as defined hereinbefore, for use as a medicament.

According to another aspect of the invention, there is provided the use of a compound of the formula I, or a pharmaceutically acceptable salt thereof, as defined hereinbefore, in the manufacture of a medicament for use as a Tie2 receptor tyrosine kinase inhibitor in a warm-blooded animal such as man.

According to another aspect of the invention, there is provided the use of a compound of the formula I, or a pharmaceutically acceptable salt thereof, as defined hereinbefore, in the manufacture of a medicament for use in the production of an anti-angiogenic effect in a warm-blooded animal such as man.

According to another aspect of the invention, there is provided the use of a compound of the formula I, or a pharmaceutically acceptable salt thereof, as defined hereinbefore in the manufacture of a medicament for use in the treatment of cancers in a warm-blooded animal such as man.

According to another aspect of the invention, there is provided the use of a compound of the formula I, or a pharmaceutically acceptable salt thereof, as defined hereinbefore in the manufacture of a medicament for use in the treatment of a cancer selected from leukaemia, breast, lung, colon, rectal, stomach, prostate, bladder, pancreas, ovarian, lymphoma, testicular, neuroblastoma, hepatic, bile duct, renal cell, uterine, thyroid and skin cancer in a warm-blooded animal such as man.

According to another aspect of the invention there is provided a method of inhibiting Tie2 receptor tyrosine kinase in a warm-blooded animal, such as man, in need of such treatment, which comprises administering to said animal an effective amount of a compound of the formula I, or a pharmaceutically acceptable salt thereof, as defined hereinbefore.

According to another aspect of the invention there is provided a method for producing an anti-angiogenic effect in a warm-blooded animal, such as man, in need of such treatment, which comprises administering to said animal an effective amount of a compound of the formula I, or a pharmaceutically acceptable salt thereof, as defined hereinbefore.

According to another aspect of the invention there is provided a method of treating cancers in a warm-blooded animal, such as man, in need of such treatment, which comprises administering to said animal an effective amount of a compound of the formula I, or a pharmaceutically acceptable salt thereof, as defined hereinbefore.

According to another aspect of the invention there is provided a method of treating a cancer selected from leukaemia, breast, lung, colon, rectal, stomach, prostate, bladder, pancreas, ovarian, lymphoma, testicular, neuroblastoma, hepatic, bile duct, renal cell, uterine, thyroid or skin cancer, in a warm-blooded animal, such as man, in need of such treatment, which comprises administering to said animal an effective amount of a compound of the formula I, or a pharmaceutically acceptable salt thereof, as defined hereinbefore.

According to another aspect of the invention there is provided a compound of the formula I, or a pharmaceutically acceptable salt thereof, as defined hereinbefore, for use in inhibiting Tie2 receptor tyrosine kinase in a warm-blooded animal, such as man.

According to another aspect of the invention there is provided a compound of the formula I, or a pharmaceutically acceptable salt thereof, as defined hereinbefore, for use in producing an anti-angiogenic effect in a warm-blooded animal, such as man.

According to another aspect of the invention there is provided a compound of the formula I, or a pharmaceutically acceptable salt thereof, as defined hereinbefore, for use in the treatment of cancer.

According to another aspect of the invention there is provided a compound of the formula I, or a pharmaceutically acceptable salt thereof, as defined hereinbefore, for use in the treatment of a cancer selected from leukaemia, breast, lung, colon, rectal, stomach, prostate, bladder, pancreas, ovarian, lymphoma, testicular, neuroblastoma, hepatic, bile duct, renal cell, uterine, thyroid or skin cancer.

As hereinbefore mentioned it is further expected that a compound of the present invention will possess activity against other diseases mediated by undesirable or pathological angiogenesis including psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

The anti-angiogenic activity defined herein may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may include one or more of the following categories of anti-tumour agents:

(i) anti-invasion agents (for example metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl)amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5 α-reductase such as finasteride;

(iv) inhibitors of growth factor function, for example such inhibitors include growth factor antibodies, growth factor receptor antibodies, farnesyl transferase inhibitors, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents that work by different mechanisms to those defined hereinbefore, such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin);

(vi) biotherapeutic therapeutic approaches for example those which use peptides or proteins (such as antibodies or soluble external receptor domain constructions) which either sequest receptor ligands, block ligand binding to receptor or decrease receptor signalling (e.g. due to enhanced receptor degradation or lowered expression levels)

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically active agent within its approved dosage range.

According to this aspect of the invention there is provided a pharmaceutical product comprising a compound of the formula I as defined hereinbefore and an additional anti-tumour substance as defined hereinbefore for the conjoint treatment of cancer.

In addition to their use in therapeutic medicine, the compounds of formula I and their pharmaceutically acceptable salts, are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

The invention will now be illustrated by the following non-limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LC-MS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra (MS) were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is MH$^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:
AcOH Acetic acid
AIBN 2,2'-Azobisisobutyronitrile
DCM Dichloromethane
DIPEA Diisopropylethylamine
DMA N,N-Dimethylacetamide
DMF N,N-Dimethylformamide
DMSO Dimethylsulfoxide
DMTMM 4-(4,6-Dimethoxy-1,3,5-triazin-2-yl)-4-methyl-morpholin-4-ium chloride
dppf 1,1'-Bis(diphenylphosphino)ferrocene
EtOAc Ethylacetate
HATU O-(7-Azabenzotriazol-1-yl)-N,N,N',N'-tetramethyluronium hexafluorophosphate
$^i$PrMgCl Isopropylmagnesium chloride
LDA Lithium diisopropylamide
LHMDS Lithium bis(trimethylsilyl) amide
m-CPBA meta-Chloroperbenzoic acid
MeOH Methanol
MeCN Acetonitrile
MCX Mixed cation exchange resin
MTBE Methyl tert-butyl ether
LCMS Liquid Chromatograpy—Mass Spectrometry
NMP 1-Methyl-2-pyrrolidinone
PhTosMIC α-Tosylbenzyl isocyanide
$POCl_3$ Phosphorus oxychloride
RPHPLC Reversed phase high peformance liquid chromatography
TFA Trifluoroacetic acid
THF Tetrahydrofuran xvii) where a synthesis is described as leading to an acid addition salt (e.g. HCl salt), no comment is made on the stoichiometry of this salt. Unless otherwise stated, all NMR data is reported on free-base material, with isolated salts converted to the free-base form prior to characterisation.

EXAMPLE 1

N-{3-[5-(4-Aminothieno[2,3-d]pyrimidin-6-yl)-1-methyl-1H-imidazol-4-yl]phenyl}-N'-(3-fluorophenol)urea 6-[4-(3-Aminophenyl)-1-methyl-1H-imidazol-5-yl]thieno[2,3-d]pyrimidin-4-amine (64 mg) in anhydrous tetrahydrofuran (10 mL) was added to 3-fluorophenyl isocyanate (41 mg) and stirred under an inert atmosphere at ambient temperature for 1 hr. The mixture was diluted with DCM (5 mL) then purified by chromatography on silica eluting with a gradient of 0-50% EtOAc/DCM, then 0-20% MeOH/DCM to give the title compound as a solid (71 mg, 77%); $^1$H NMR (DMSOd6) δ 3.65 (s, 3H), 6.83 (m, 1H), 7.15 (m, 2H), 7.25 (m, 1H), 7.35 (m, 2H), 7.48 (m, 1H), 7.68 (s,br 2H), 7.72 (s, 1H), 7.80 (m, 1H), 7.99 (s, 1H), 8.39 (s, 1H), 8.79 (s, 1H), 8.89 (s,1H);
MS m/e MH$^+$ 460.

EXAMPLE 2

N-{3-[5-(4-aminothieno[2,3-d]pyrimidin-6-yl)-1-methyl-1H-imidazol-4-yl]phenyl}-N'-(2-fluorophenyl)urea 6-[4-(3-Aminophenyl)-1-methyl-1H-imidazol-5-yl]thieno[2,3-d]pyrimidin-4-amine (64 mg) in anhydrous tetrahydrofuran (10 mL) was added to 2-fluorophenyl isocyanate (34 mg) and stirred under an inert atmosphere at ambient temperature for 1 hr. The mixture was diluted with DCM (5 mL) then purified by chromatography on silica eluting with a gradient of 0-50% EtOAc/DCM, then 0-50% MeOH (containing 1% concentrated aqueous amnmonia)/DCM to give the title compound as a solid (76 mg, 82%).
$^1$H NMR (DMSOd6) δ 3.58 (s, 3H), 7.00 (m, 1H), 7.20 (m, 5H), 7.58 (s,br 2H), 7.68 (s, 1H), 7.78 (m, 1H), 7.91 (s, 1H), 8.04 (m, 1H), 8.34 (s, 1H), 8.45 (s,1H), 9.00 (s, 1H);
MS m/e MH$^+$ 460.

The starting material was prepared as follows:—

Intermediate 1

{(3-iodophenyl)[(4-methylphenyl)sulfonyl]methyl}formamide

Trimethylsilylchloride (9.1 mL) was added to a stirred solution of 3-iodobenzaldehyde (15.1 g) and formamide (6.5 mL) in MeCN (34 mL) and toluene (34 mL) under an inert atmosphere. The reaction was then heated at 50° C. for 5 hours. Toluene sulfinic acid (15.3 g) was added and the reaction mixture was heated at 50° C. for a further 5 hours. The reaction mixture was cooled to ambient temperature, methyl t-butylether (55 mL) was added and stirred for 5 minutes. Water (275 mL) was added, the reaction cooled to 0° C. and stirred for 1 hour. The solid was filtered and the reaction flask was washed with MTBE (2×35 mL) and poured over the filtered cake. The solid was dried in a vacuum oven at 60° C. for 10 hours to afford impure title compound as a solid (14 g, 51%) which was used without further purification. A small sample was crystallised from EtOH;
$^1$H NMR (DMSO-d6) for major (6:1) rotamer δ; 2.43 (s, 3H), 6.42 (d, 1H), 7.15-8.00 (m, 9H), 9.73 (d, 1H).
MS m/e MH$^+$ 416.

Intermediate 2

(3-iodophenyl)(isocyano)methyl 4-methylphenyl sulfone $POCl_3$ (3.05 mL) was added to a stirred solution of {(3-iodophenyl)[(4-methylphenyl)sulfonyl]methyl}formamide (6.23 g) in dry THF (35 mL) at 25° C. and stirred for 5 minutes. The reaction mixture was cooled to 0° C. and $Et_3N$ (13.7 mL) was added dropwise over 45 minutes, keeping the internal temperature below 10° C. The reaction mixture was allowed to stir at 5-10° C. for a further 45 minutes. EtOAc (140 mL) and water (140 mL) was added and then stirred for 5 minutes. The organic phase was washed with water (2×140 mL), NaHCO3 (sat. aq., 140 mL) and then brine (140 mL). The organic phase was concentrated in vacuo to afford a dark brown gum. This was then passed through a pad of silica washing with DCM and concentrated in vacuo to afford a dark brown gum (ca. 70% pure 3.5 g, 58%);
$^1$H NMR ($CDCl_3$) δ 2.42 (s, 3H), 5.45 (s, 1H), 7.00-7.75 (m, 8H);
MS m/e (M-H)$^-$ 396.

Intermediate 3

4-(Methylthio)thieno[2,3-d]pyrimidine-6-carbaldehyde 4-(Methylthio)thieno[2,3-d]pyrimidine (*J. Heterocycl. Chem.* 1975, 12, 921-924) (1 g) in THF (5 mL) was added to a preformed solution of LDA [BuLi (1.6M in hexanes, 3.8 mL) and di-isopropylamine (0.85 mL)] in THF (20 mL) at −78° C. The reaction mixture was allowed to stir for 1 hour at −78° C. and then DMF (1.1 mL) was added. The reaction mixture was stirred at −78° C. for 30 minutes then allowed to warm to ambient temperature and stirred for a further 3 hours. The reaction mixture was diluted with water and the product was extracted with EtOAc (4×30 mL). The combined organic extracts were washed with brine (30 mL), dried (MgSO$_4$), filtered and concentrated in vacuo. Purification by flash chromatography on silica eluting with DCM afforded the title compound as a white solid (1.17 g, 51%);

$^1$H NMR (CDCl$_3$) δ 2.76 (s, 3H), 8.03 (s, 1H), 8.90 (s, 1H), 10.10 (s, 1H);

MS m/e MH$^+$ 211.

Intermediate 4

N-[4-(methylthio)thieno[2,3-d]pyrimidin-6-ylmethylidene]methanamine 4-(Methylthio)thieno[2,3-d]pyrimidine-6-carbaldehyde (13 g), methylamine (33% in EtOH, 20.6 mL) and anhydrous MgSO$_4$ (20 g) was stirred in DCM (465 ml) for 2 days at ambient temperature under an inert atmosphere. The reaction mixture was filtered then concentrated in vacuo to afford the title compound as a brown solid (13.8 g, 100%);

$^1$H NMR (DMSOd6) δ 2.70 (s, 3H), 3.45 (s, 3H), 7.82 (s, 1H), 8.62 (s, 1H), 8.89 (s, 1H).

Intermediate 5

6-[4-(3-iodophenyl)-1-methyl-1H-imidazol-5-yl]-4-(methylthio)thieno[2,3-d]pyrimidine N-[4-(methylthio)thieno[2,3-d[pyrimidin-6-ylmethylidene]methanamine (1.0 g), (3-iodophenyl)(isocyano)methyl 4-methylphenyl sulfone (3.4 g, 70% pure) and piperazine (0.77 g) in THF (80 mL) was stirred under an inert atmosphere for 4 days. The reaction mixture was concentrated, diluted with water, and extracted with EtOAc. The extract was washed with saturated aqueous NaHCO$_3$, dried (MgSO$_4$), filtered and concentrated in vacuo. Purification by chromatography on silica eluting with a gradient of 0-100% EtOAc/DCM then 0-5% MeOH/DCM, followed by crystallization from EtOH, gave the title product as a solid (1.2 g, 57%.)

$^1$H NMR (DMSO-d6) δ 2.68 (s, 3H), 3.60 (s, 3H), 7.04 (t, 1H), 7.37 (d, 1H), 7.55 (d, 1H), 7.70 (s, 1H), 7.94 (m, 2H), 8.89 (s, 1H);

MS m/e MH$^+$ 465.

Intermediate 6

6-[4-(3-iodophenyl)-1-methyl-1H-imidazol-5-yl]-4-(methylsulfonyl)thieno[2,3-d]pyrimidine m-CPBA (70-75%, 399 mg) was added to a solution of 6-[4-(3-iodophenyl)-1-methyl-1H-imidazol-5-yl]-4-(methylthio)thieno[2,3-d]pyrimidine (300 mg) in DCM (20 mL) and stirred for 24 hours. Aqueous sodium metabisulfite was added and the mixture extracted with DCM. The organic phase was washed with saturated aqueous NaHCO$_3$, dried (MgSO$_4$), filtered and concentrated in vacuo to give the title compound as a yellow solid (220 mg, 68%);

$^1$H NMR (DMSO-d6) δ 3.50 (s, 3H), 3.66 (s, 3H), 7.04 (t, 1H), 7.38 (d, 1H), 7.59 (d, 1H), 8.00 (m, 3H), 9.34 (s, 1H);

MS m/e MH$^+$ 497.

Intermediate 7

6-[4-(3-Iodophenyl)-1-methyl-1H-imidazol-5-yl]thieno[2,3-d]pyrimidin-4-amine

6-[4-(3-iodophenyl)-1-methyl-1H-imidazol-5-yl]-4-(methylsulfonyl)thieno[2,3-d]pyrimidine (200 mg) and concentrated aqueous ammonia (5 mL) was stirred in 1,4-dioxane (15 mL) for 17 hours. The solvent was evaporated and the residue purified by chromatography on silica eluting with a gradient of 0-50% EtOAc/DCM then 0-20% MeOH/DCM to give the title compound as a colourless solid (136 mg, 78%);

$^1$H NMR (DMSO-d6) δ 3.58 (s, 3H), 7.06 (t, 1H), 7.42 (d, 1H), 7.56 (d, 1H), 7.65 (m, 3H), 7.95 (m, 2H), 8.32 (s, 1H).

MS m/e MH$^+$ 434.

Intermediate 8

6-(4-{3-[(Diphenylmethylene)amino]phenyl}-1-methyl-1H-imidazol-5-yl)thieno[2,3-d]pyrimidin-4-amine 6-[4-(3-Iodophenyl)-1-methyl-1H-imidazol-5-yl]thieno[2,3-d]pyrimidin-4-amine (860 mg), benzophenone imine (540 mg), 1,1'-bis(diphenylphosphino)ferrocene (120 mg), bis(benzylideneacetone)palladium (100 mg) and sodium tert-butoxide (960 mg) in dioxane (40 mL) was degassed then heated at 90° C. under an inert atmosphere. After 17 hours the reaction mixture was cooled, diluted with water (50 mL), extracted with EtOAc (2×30 mL), organic extracts washed with brine, dried, filtered and concentrated in vacuo. Purification by flash chromatography on silica eluting with DCM/MeOH (0-10%) gave the title compound (0.48 g, 50%);

$^1$H NMR (CDCl$_3$) δ 3.32 (s, 3H), 5.75 (bs, 2H), 6.40-6.45 (m, 1H), 6.85-6.94 (m, 4H), 6.83-7.15 (m, 5H), 7.28-7.32 (m, 2H), 7.35-7.40 (m, 1H), 7.48 (s, 1H), 7.57-7.62 (m, 2H), 8.40 (s, 1H);

MS m/e MH$^+$ 487.

Intermediate 9

6-[4-(3-Aminophenyl)-1-methyl-1H-imidazol-5-yl]thieno[2,3-d]pyrimidin-4-amine

2M HCl (0.75 mL) was added to a solution of 6-(4-{3-[(diphenylmethylene)amino]phenyl}-1-methyl-1H-imidazol-5-yl)thieno[2,3-d]pyrimidin-4-amine (0.45 g) in THF (15 mL), stirred for 10 mins, then partitioned between water and EtOAc. The aqueous layer was separated, basified to pH9 with concentrated aqueous ammonia, extracted with DCM (3×30 mL), combined organics dried, filtered and concentrated in vacuo to give the title compound as a colourless solid (0.33 g, 100%);

$^1$H NMR (DMSO-d$_6$) δ 3.54 (s, 3H), 4.96 (bs, 2H), 6.36-6.39 (m, 1H), 6.55-6.57 (m, 1H), 6.83-6.88 (m, 2H), 7.56 (bs, 2H), 7.59 (s, 1H), 7.82 (s, 1H), 8.28 (s, 1H);

MS m/e MH$^+$ 323.

The invention claimed is:
1. A compound of the formula I:

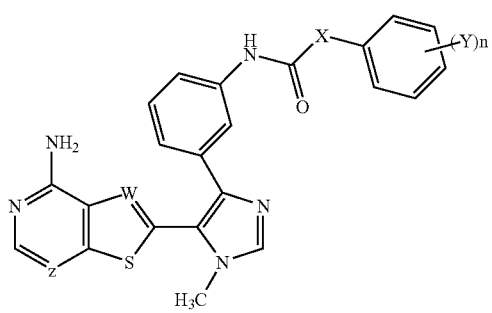

Formula I wherein:
Z is selected from N and CH;
W is selected from N and CH;
X is selected from NH and CH$_2$;
Y is selected from F, Cl, Br and I; and
n is 1, 2 or 3;
or pharmaceutically acceptable salt thereof.

2. A compound of the formula I according to claim 1, wherein Z is N, or pharmaceutically acceptable salt thereof.

3. A compound of the formula I to claim 1 wherein Y is selected from F and/or Cl, or pharmaceutically acceptable salt thereof.

4. A compound of the formula I according to claim 1, selected from one or more of the following:

N-{3-[5-(4-aminothieno[2,3-d]pyrimidin-6-yl)-1-methyl-1H-imidazol-4-yl]phenyl}-N'-(3-fluorophenyl)urea;
N-{3-[5-(4-aminothieno[2,3-d]pyrimidin-6-yl)-1-methyl-1H-imidazol-4-yl]phenyl}-N'-(2-fluorophenyl)urea;
N-{3-[5-(4-aminothieno[2,3-d]pyrimidin-6-yl)-1-methyl-1H-imidazol-4-yl]phenyl}-N'-(3-chlorophenyl)urea;
N-{3-[5-(4-aminothieno[2,3-d]pyrimidin-6-yl)-1-methyl-1H-imidazol-4-yl]phenyl}-N'-(2-chlorophenyl)urea;
N-{3-[5-(4-aminothieno[2,3-d]pyrimidin-6-yl)-1-methyl-1H-imidazol-4-yl]phenyl}-2-(3-fluorophenyl)acetamide;
N-{3-[5-(4-aminothieno[2,3-d]pyrimidin-6-yl)-1-methyl-1H-imidazol-4-yl]phenyl}-2-(2-fluorophenyl)acetamide;
N-{3-[5-(4-aminothieno[2,3-d]pyrimidin-6-yl)-1-methyl-1H-imidazol-4-yl]phenyl}-2-(3-chlorophenyl)acetamide;
N-{3-[5-(4-aminothieno[2,3-d]pyrimidin-6-yl)-1-methyl-1H-imidazol-4-yl]phenyl}-2'-(2-chlorophenyl)acetamide;
N-{3-[5-(4-aminothiazolo[2,3-d]pyrimidin-6-yl)-1-methyl-1H-imidazol-4-yl]phenyl}-N'-(3-fluorophenyl)urea;
N-{3-[5-(4-aminothiazolo[2,3-d]pyrimidin-6-yl)-1-methyl-1H-imidazol-4-yl]phenyl}-N'-(2-fluorophenyl)urea;
N-{3-[5-(4-aminothiazolo[2,3-d]pyrimidin-6-yl)-1-methyl-1H-imidazol-4-yl]phenyl}-N'-(3-chlorophenyl)urea;
N-{3-[5-(4-aminothiazolo[2,3-d]pyrimidin-6-yl)-1-methyl-1H-imidazol-4-yl]phenyl}-N'-(2-chlorophenyl)urea;
N-{3-[5-(4-aminothiazolo[2,3-d]pyrimidin-6-yl)-1-methyl-1H-imidazol-4-yl]phenyl}-2-(3-fluorophenyl)acetamide;
N-{3-[5-(4-aminothiazolo[2,3-d]pyrimidin-6-yl)-1-methyl-1H-imidazol-4-yl]phenyl}-2-(2-fluorophenyl)acetamide;
N-{3-[5-(4-aminothiazolo[2,3-d]pyrimidin-6-yl)-1-methyl-1H-imidazol-4-yl]phenyl}-2-(3-chlorophenyl)acetamide;
N-{3-[5-(4-aminothiazolo[2,3-d]pyrimidin-6-yl)-1-methyl-1H-imidazol-4-yl]phenyl}-2-(2-chlorophenyl)acetamide;
or pharmaceutically acceptable salt thereof.

5. A pharmaceutical composition comprising a compound of the formula I, or a pharmaceutically acceptable salt thereof, as defined in claim 1 in association with a pharmaceutically acceptable diluent or carrier.

6. A process for preparing a compound of formula I according to claim 1, or a salt or solvate thereof, wherein X is NH and Z, W, Y and n are as defined in claim 1, which process comprises of reacting an amine of the formula II with an isocyanate of the formula III
and thereafter if necessary:

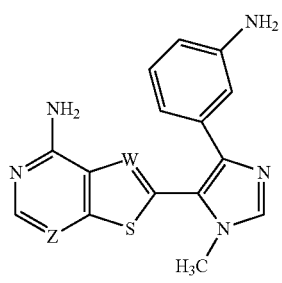

Formula II

Formula III i) converting a compound of the formula (I) into another compound of the formula (I);
ii) forming a pharmaceutically acceptable salt.

* * * * *